July 24, 1973 H. C. BROWNELL Plant Pat. 3,375
ROSE PLANT
Filed Dec. 15, 1971
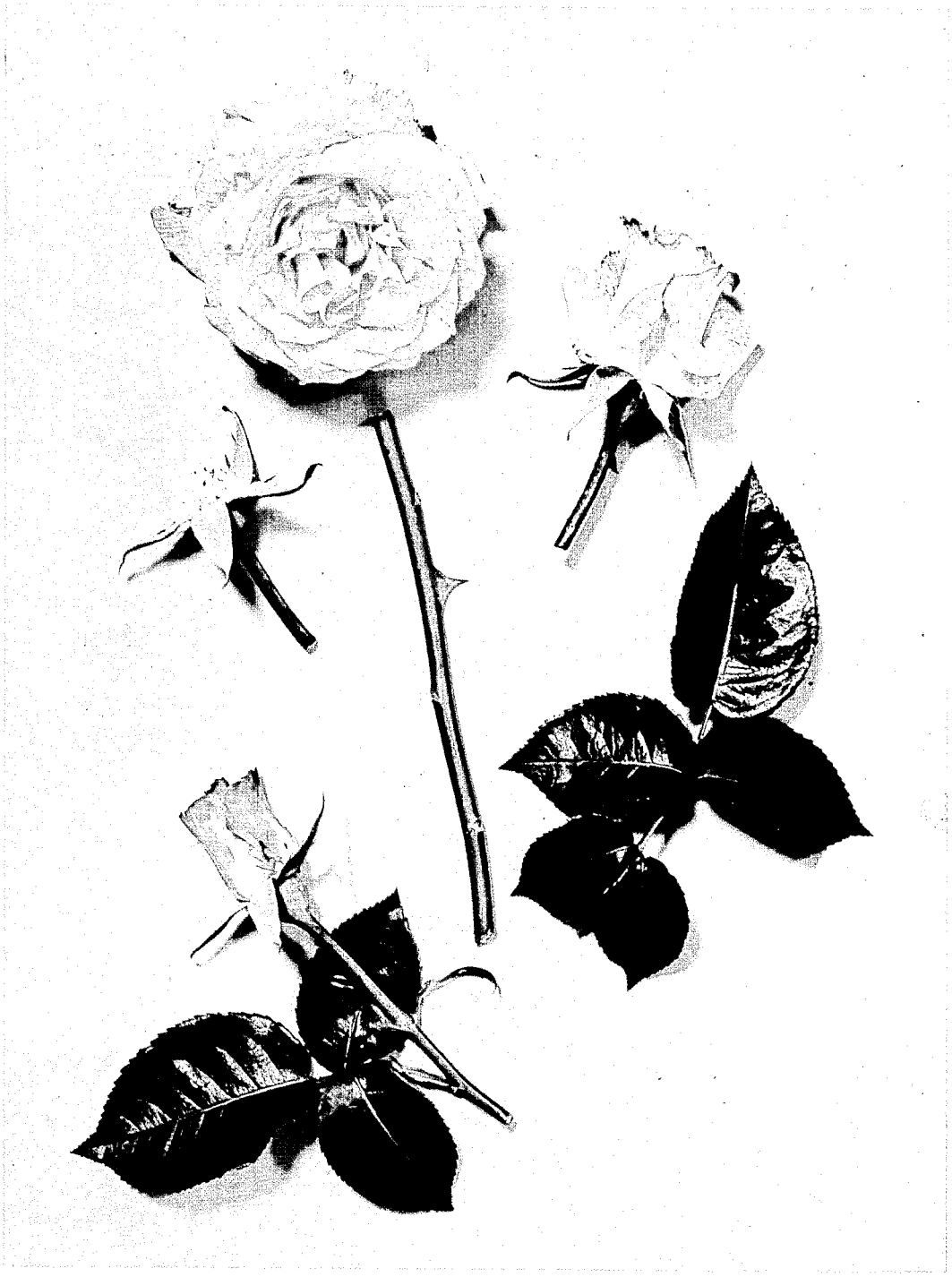
Inventor
Herbert C. Brownell United States Patent Office Plant Pat. 3,375
Patented July 24, 1973

3,375
ROSE PLANT

Herbert C. Brownell, Little Compton, R.I. 02837

Filed Dec. 15, 1971, Ser. No. 208,485
Int. Cl. A01h 5/00
U.S. Cl. Plt.—11 1 Claim My invention relates to roses and especially to a new, original and distinct variety of the class known commercially as "hybrid tea" and is a variant in that class, being a *Rosa wichuraiana* hybrid tea hybrid, produced by me and under my direction in the breeding grounds of my research gardens in Little Compton, R.I., by selection of variety variations and by cross pollination, which can be and has been asexually reproduced.

My new rose plant is new as to the following characteristics and especially as to their joint association with the characteristics inherited from *Rosa wichuraiana*, of hardiness, or immunity from serious injury on account of cold temperatures prevailing in certain parts of the northern United States;

The etched pink overlaid on yellow (ordinary dictionary definition) of its petals in combination with the unique brilliance thereof and their tendency to hold these colors under exposure, fading only very slightly under direct rays of the sun.

The novelty and variation within certain definite limits of the form of the bloom, the recurl of the petals as the flower opens, its character of holding its form for a long time and the petalage of the flowers;

Its unusual abundance of flowers at bloom time and after early bloom time until frost;

Its character of ascending in height by recurrent branching and progressively longer stems from the base.

The character of producing many seven leafleted leaves, which character seldom has obtained on hybrid teas not having *Rosa wichuraiana* ancestry.

And especially its characteristic of freedom from premature defoliation by blackspot, under certain definite conditions of exposure, without any cultural control.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Wilson's Horticultural Colour Chart, except where general color terms of ordinary dictionary significance are obvious:

Type: Hardy; bush; outdoor; seedling; for cut flowers and garden decoration.
Class: Hybrid tea.
Breeding: Seedling.
*Seed parent.*—Helen Hayes—Plant Pat. No. 1509.
*Pollen parent.*—Traviata—Plant Pat. No. 2283.
Propagation: Holds its distinguishing characterstics through succeeding propagations by budding.

*Flower*

Locality where grown and observed: Little Campton, R.I., U.S.A.
Flowers borne: Singly and in clusters on stems of medium length and normal strength.
Quantity of bloom: Abundant, outdoors.

Continuity: Continuous during growing season until frost.
Fragrance: Very intense.
Bud:
*Peduncle.*—Average length; medium caliper; very few red hairs. Color—Lettuce Green 861/3.
*Before calyx breaks.*—Size—medium. Form—pointed; with foliaceous parts extending beyond the tip of the bud equal to ½ or more of its length. Color—Scheeles Green 860/1.
*As calyx breaks.*—Color (outside of petal)—Currant Red 821.
*As first petal opens.*—Size—medium. Form—globular. Color: Outside—Currant Red 821. Inside—Currant Red 821/1.
Bloom:
*Size (when fully open).*—Medium, about 4½ inches in diameter.
*Petalage.*—Double; from 50 to 55 petals arranged regularly.
*Form.*—Globular to recurl as bloom opens.
Petals:
*Texture.*—Thick; not satiny.
*Shape.*—Orbiculate; notches on outer petals.

This description of a newly open flower was made from a rose grown outdoors at Little Compton, R.I., in the month of September.

*Color.*—Outer petal: outside surface—Chinese Coral 614/3 changing to a Empire Yellow 603/1 at the base of the petal; inside surface—Carmine China Rose 024/1.
*Flower longevity.*—On bush in graden 5 or 6 days in September. Cut roses grown outdoors and kept at living room temperature 3 or 4 days in September.

*Reproductive organs*

Stamens: Average number; arranged irregular.
Filaments: Average number; most with anthers of average size varying greatly in length. Color—Chinese Yellow 606/1.
Anthers: All open at once; medium sized. Color—Maize Yellow 607.
Pollen: Abundant. Color—Spanish Orange 010.
Pistils: Abundant; irregularly arranged.
Styles: Uneven; medium length; from thin to average caliper. Color—near Amber Yellow 505/3.
Stigma: Color—Amber Yellow 505/1.
Ovaries: All enclosed in calyx.
Hips: Medium size; globular; smooth. Color (mature)—Pod Green 061.
Sepals: Pointed; permanent. Color: Outside—Pod Green 061/1. Inside—Lavender Green 000761/1.
Seeds: Few; about six or seven to a hip. Fairly large size.

*Plant*

Foliage:
*Leaves.*—Compound of usually 5 to 7 leaflets; normal quantity; medium to large size.
*Leaflets.*—Shape—obovate. Base—round; edges very finely serrated.
*Color.*—Upper surface—Spinach Green 0860; under surface—Scheeles Green 860.
*Rachis.*—Average size. Upper side—grooved; with smooth edges. Under side—smooth.

*Stipules.*—Short to medium; average width; points of medium length, the upper of which normally form an angle of about 90 degrees.

*Disease resistance.*—Better-than-average resistance to black-spot and mildew as compared with other varieties grown under comparable conditions at Little Compton, R.I.

Growth:

*Habit.*—Bushy; upright-spreading; much-branched.

*Growth.*—From very free to vigorous.

*Canes.*—Medium caliper.

*Main stems.*—Color—Fern Green 0862. Prickles—few; moderates sizes; slightly hooked downward; color—Garnet Brown 00918. Hairs—none.

*Branches.*—Color—Lettuce Green 861/1 with overlay of Cardinal Red 821/1. Medium pickles—several; short; hooked slightly downward; color—Cardinal Red 822/1. Hairs—none.

I claim:

1. A new and distinct variety of rose plant of the hybrid tea type, substantially as herein shown and described, characterized particularly as to novelty by its vigorous habit of growth, abundant foliage, its resistance to mildew and blackspot, and its ability to withstand moderate subzero temperatures in combination with its hybrid tea character and its *Rosa wichuraiana* ancestry.

No references cited

ROBERT E. BAGWILL, Primary Examiner